(12) United States Patent
Foote

(10) Patent No.: US 6,371,932 B1
(45) Date of Patent: Apr. 16, 2002

(54) APPENDAGE CORRECTION DEVICE

(75) Inventor: Brian Foote, Lancashire (GB)

(73) Assignee: Dynamic Health Care Limited, Southport (GB)

(*) Notice: Subject to any disclaimer, the term of this patent is extended or adjusted under 35 U.S.C. 154(b) by 0 days.

(21) Appl. No.: 09/190,665

(22) Filed: Nov. 12, 1998

(30) Foreign Application Priority Data

Apr. 15, 1998 (GB) ............................................. 9807858

(51) Int. Cl.$^7$ ............................... A61F 5/00; A61F 5/37
(52) U.S. Cl. ........................... 602/22; 602/20; 128/880
(58) Field of Search .............................. 602/20–22, 32, 602/36; 128/878–880; 601/40, 33; 482/44, 47, 48

(56) References Cited

U.S. PATENT DOCUMENTS

| | | | | |
|---|---|---|---|---|
| 1,072,369 A | * | 9/1913 | Spahn | 602/26 X |
| 2,222,180 A | * | 11/1940 | Marsh | 482/48 X |
| 2,439,100 A | * | 4/1948 | Richards | 602/28 |
| 3,782,719 A | * | 1/1974 | Kuhlman | 602/5 |
| 4,602,620 A | * | 7/1986 | Marx | 602/22 |
| 4,765,320 A | * | 8/1988 | Lindemann et al. | 602/22 |
| 4,790,300 A | | 12/1988 | Marx | |
| 4,790,301 A | * | 12/1988 | Silfverskiold | 602/22 |
| 4,945,902 A | * | 8/1990 | Dorer | 602/38 |
| 4,949,711 A | | 8/1990 | Gyovai et al. | |
| 4,955,370 A | * | 9/1990 | Pettine | 602/28 |
| 5,382,224 A | * | 1/1995 | Spangler | 602/28 X |
| 5,514,052 A | * | 5/1996 | Charles | 482/47 |
| 6,063,087 A | * | 5/2000 | Agee | 602/21 |
| 6,093,162 A | * | 7/2000 | Fairleigh | 602/22 |

FOREIGN PATENT DOCUMENTS

GB   2 204 492 A   11/1988

\* cited by examiner

Primary Examiner—Denise Pothier
(74) Attorney, Agent, or Firm—Woodard, Emhardt, Naughton Moriarty & McNett

(57) ABSTRACT

There is disclosed a medical correction device for correcting the attitude of a finger of the user which is prone to adopting an undesirable attitude, as is the case, for example, in conditions such as clawed fingers. The device comprises a base portion that can secure the user's hand or wrist to which a resilient member such as a coiled spring, and a rotatable projection member are attached. The resilient member is also attached to the rotatable projection member and subtends an angle therewith. In use, relative rotation between the projection member and the base portion gives rise to a restoring force exerted by the resilient member, a component of which acts on the finger. As the user bends his or her finger, the projection member rotates away from the base portion and reduces the angle subtended between the projection member and the resilient member. The component of the restoring force transmitted by the projection member back to the base portion is increased while the component of the restoring force which acts on the finger is reduced. The correcting effect of the device is therefore reduced and can be eliminated when the finger is significantly angled with respect to the portion of the user to which the finger is attached.

9 Claims, 2 Drawing Sheets

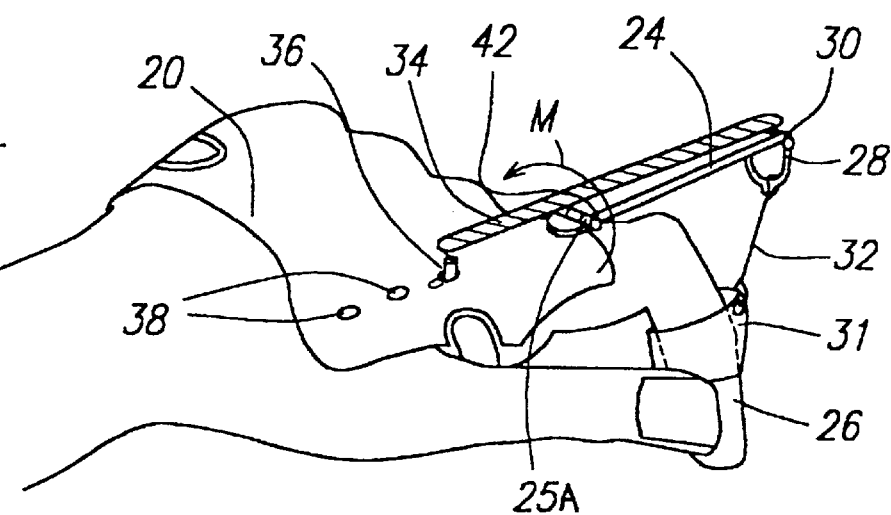
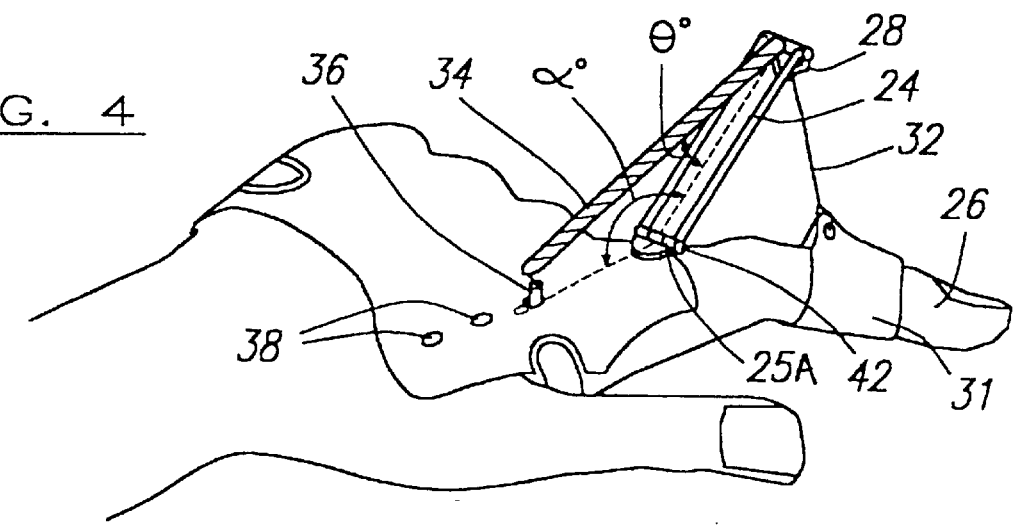
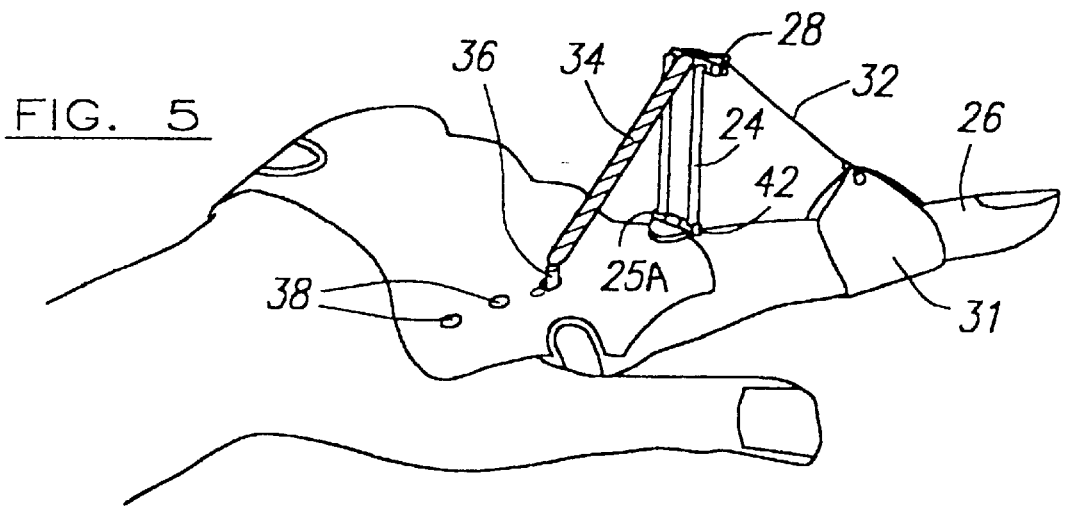

APPENDAGE CORRECTION DEVICE

BACKGROUND OF THE INVENTION

This invention relates to an appendage correction device, in particular to an appendage correction device which is spring biased for correcting the attitude of a particular appendage of a human or mammal with respect to the particular portion of that human or mammal to which said appendage is attached. Examples include wrists, feet or other limbs, or one or more of a plurality of digits, or optionally the head of a human or mammal which are all prone to adopt incorrect or deficient attitudes.

A previous type of splint for extending a user's fingers from a clawed position is shown in FIG. 1. This type of splint comprised a rigid back portion 10 to be secured to the back of a user's hand and along their wrist. The back portion 10 is typically made of plastic and is preformed to follow the shape of a user's hand and wrist.

One end of a spring 12 is secured at the end of the back portion 10 closest to the user's elbow. The other end of the spring is secured to a piece of fishing line 14, which itself is secured to a sling 16 placed over the user's finger. The fishing line 14 is run over a pulley 18 which is secured to a raised lip 20 at the end of the back portion 10 closest to the user's fingers. The length of the spring 12 and fishing line 14 are arranged so that tension is exerted on the user's finger to straighten the finger to improve the clawing condition. The splint is secured to the user's wrist with straps 22. Typical examples of the splints described above can be seen in U.S. Pat. No. 4,949,711 (Gyovai et al.) and U.S. Pat. No. 4,765,320 (Lindemann et al.). An example of a foot splint working on similar principles is shown in U.S. Pat. No. 5,382,224 (Spangler).

The fundamental disadvantage with splints of the type described above arises from the simple physics associated with Hooke's law for the extension of springs, being $F=kx$, where F is the force required to extend the spring, x is the extension of the spring under the said force, and k is the spring constant. When a user attempts to grip an item by curling his fingers, he has to apply a muscular force to overcome the resistance of the spring before his fingers will curl. In accordance with Hooke's law, this force increases as the spring extends and thus renders the gripping and manipulation of items difficult, especially small items where one or more of the fingers of the user may be required to be curled through 90° such that the fingers are perpendicular to the palm of the had or through a even greater angle.

Also, the grip cannot be maintained for any great length of time because a continuous force must be used to maintain the extension of the spring. Typically, such a device becomes painful to wear after one or two hours.

A further disadvantage of the existing splints is the gradual deterioration of their therapeutic effect as the fingers are straightened. It is most preferable for splints to exert only a nominal correcting force on the fingers at first to avoid inflicting excessive pain and discomfort caused by immediately applying a large correcting force, and thereafter steadily increase the correcting force. However, existing splints function in the entirely opposite manner as they are usually first applied when the fingers are completely clawed, and the springs which apply the correcting force to the fingers are therefore at their maximum extension. Henceforth as the fingers are straightened, the spring extension reduces as does the correcting force, hence necessitating the use of a number of different springs of different lengths or spring constants which can be successively affixed to the splint and to the finger slings after the attitude of the fingers have been corrected by an appropriate amount. Only in this manner can a suitable correcting force be continually applied to the fingers.

It is commonly believed that utilisation of the deficient limbs or digits during the period of correction is therapeutic and can reduce the time taken to effect the correction. Existing splints do not offer the facility for utilising the fingers because the wearer is dissuaded from so utilising his fingers on account of the increased force required to move same, and concomitantly the increased pain and discomfort which may be associated with such movement.

It can be appreciated from the above that existing splints are cumbersome and unwieldy, and require the continual changing of springs as the deficiency of the user is corrected. This means that the user is required to return to hospital periodically which is undesirable. Ultimately, existing splints are so troublesome to users that they are often completely removed and discarded by the user who would rather suffer the problems associated with a clawed hand than continually wear the splint. Such circumstances are completely unacceptable, and the present invention has as one of its objects the mitigation of the above disadvantages.

Furthermore, this previous type of device does not allow a user to move his wrist.

SUMMARY OF THE INVENTION

According to the invention there is provided a correction device for correcting the attitude of one or more digits of a hand from a curled position into a straight condition in which said digits extend away from the palm of said hand, said device comprising a base portion having means for securing the device to the hand behind the digits, said base portion having a front edge proximate the digits and a rear edge disposed at least partially around the hand behind the digits, a projection member pivotally attached to the base portion proximate the front edge of the base portion and having a longitudinal axis, a free end and a pivoting end, a flexible sling depending from the free end of said projection member and adapted to support a digit therein, a resilient member having a longitudinal axis and being secured at a first end to said projection member at a position remote from the pivoting end of said projection member and at a second end to said base portion, the free end of said projection member being rotateable both towards and away from the rear edge of said base portion, rotation away from sad rear edge causing elastic extension of the resilient member which exerts a force on said projection member which both resists said rotation and gives rise to a couple about the pivotal attachment of said projection member which progressively decreases in magnitude as said free end of said projection member rotates away from the rear edge of said base portion and the digits supported by the sling means connected to said projection member adopt positions with greater degrees of curl, said resilient member being attached to said base portion rearwardly of the pivotal attachment of said projection member to said base portion, wherein the point of attachment of said resilient member to said base portion, the pivotal attachment of said projection member to said base portion, and the point of attachment of said resilient member to said projection member are substantially aligned when the sling means supports digits which assume the curled posit ion thus substantially eliminating the couple acting on the projection member to rotate same back towards the rear edge of said base portion.

Preferably the resilient member is linear, and the rotation of the projection member simultaneously reduces the angle subtended between said resilient member and said projection member such that the magnitude of the component of the restoring force carried by the projection member increases, whereas the magnitude of the component of the restoring force transmitted to the appendage decreases.

Preferably, for example where the device is a dynamic finger splint, the base portion is secured to the portion of the user to which the appendage is attached, and the projection member is provided with means to transfer a component of the correcting force between the base portion and the projection member exerted by the resilient member to the fingers, such as a finger sling.

The device may be a finger splint. A sling portion may be secured to the protection member. The sling portion may be finger sling. The splint may comprise a plurality of sling portions and/or resilient members.

In the second position the projection member may be beyond, preferably just beyond, alignment with the longitudinal axis of the base portion. Preferably the projection member is movable through an angle greater than 90°.

The first end of the resilient member may comprise an attachment section, which may be arranged to communicate with a corresponding attachment section of the base portion. The attachment sections may be communicating pegs and openings, or alternatively Velcro® may be used to secure the resilient member to the base portion.

The base portion may comprise a plurality of said openings, arranged longitudinally along the base portion. The resilient member may be a coiled spring.

The projection member may comprise an extension section, which may extend from a free end thereof. Preferably, the extension section extends away from the resilient member.

The sling portion may be attached to the extension section, preferably by a string or wire. The sling portion may be secured substantially perpendicularly to the extension section, to thereby reduce lateral forces between the sling portion and the user's appendage.

The base portion may be secured to the hand with straps, which may have hook and pile fastener secured thereto.

The device according to the invention has a number of advantages over currently existing splints, and these are now explained.

The component of the correcting force applied between the appendage and the portion of the user to which said appendage is attached progressively reduces and is increasingly carried by the projection member of the device as it rotates about the base portion. This is invaluable because firstly, the component of the correcting force applied to the appendage progressively increases as the projection member rotates in a direction which reduces the extension of the resilient member because as it does so, the angle between the projection member and the resilient member increases and accordingly the component of the correcting force carried by the said projection member decreases. This is desirable from a medical perspective as discussed above.

Secondly, when the projection member has rotated to such an extent that it is substantially parallel with the resilient member, almost the entire correcting force applied by the resilient member between the projection member and the base portion is carried by the projection member. The component of the Correcting force transmitted to the appendage is minimised, and in the case of a finger splint, the user can grasp and manipulate items with relative ease. Indeed, the user can be quite dextrous when the projection member is in such an orientation.

A further advantage of the device is that even when the projection member is substantially parallel with the resilient member, a slight residual force is transmitted to the appendage digit, both as a result of the bending of the resilient member over the attachment of projection member to the base, and also because the resilient member is never completely parallel with the projection member and thus a small component of the force of the spring is always transmitted to the appendage This ensures the continual efficacy of the device because unless the user is attempting to move the appendage against the action of the resilient member and so reduce the correcting force applied thereby, there remains a natural tendency for the attitude of the appendage to be corrected.

A yet further advantage of the device is that it allows a user to exercise the deficient appendage while its attitude is being corrected, and this is widely believed to be of great physiotherapeutic benefit.

Specific embodiments of the present invention will now be described, by way of example, with reference to the accompanying drawings, in which:

BRIEF DESCRIPTION OF THE DRAWINGS

FIG. 3 is a partial schematic side view of the finger splint of FIG. 2 in use;

FIG. 4 is a partial schematic side view, similar to FIG. 3 but with the finger splint in a different position;

FIG. 5 is a partial schematic side view of the finger splint in a further position;

DETAILED DISCUSSION OF THE INVENTION

Figure 1:
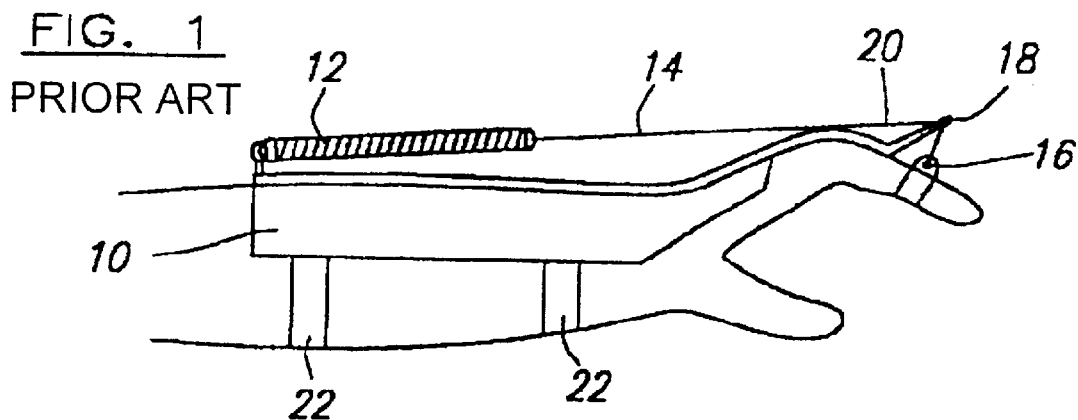
FIG. 1 is a schematic side view of a prior art splint.
Figure 2:
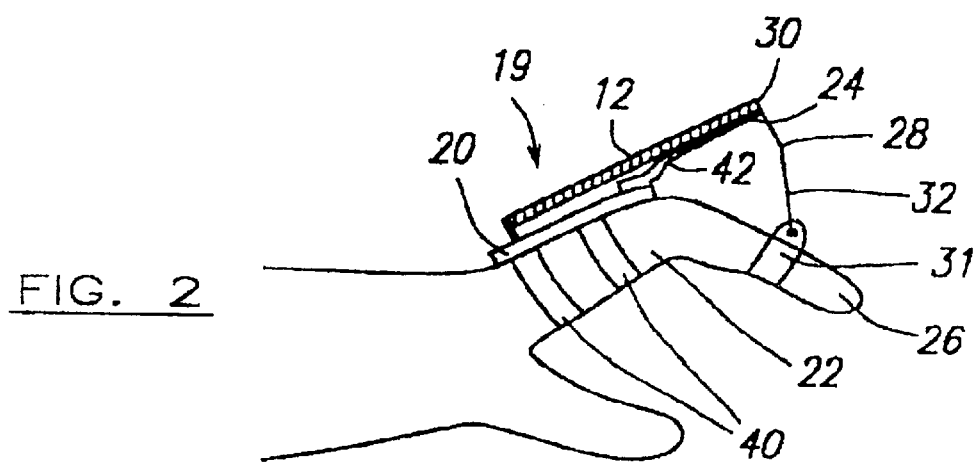
FIG. 2 is a schematic side view of a finger splint according to the present invention in use.
Figure 6:
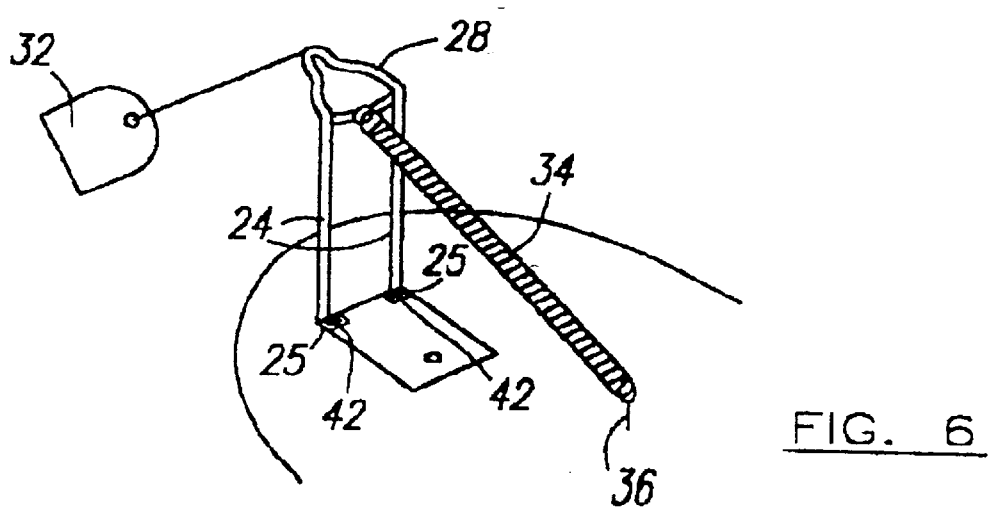
FIG. 6 is a partial schematic perspective view of the finger splint.

A finger splint 19 comprises a rigid back portion 20 sized to fit over the back of a patient's hand 22. A pivotally mounted pin 24 is secured to the end of the back portion 20 which is closest to the patient's fingers 26. The pin 24 is moveable between a position in which it is approximately perpendicular to the rigid back portion 20 (see FIG. 5) and a position in which it is approximately parallel to the rigid back portion 20 (see FIG. 3). A lever 28 extends perpendicularly from the free end 30 of the pin 24. A finger sling 31 is secured to the free end of the lever 28 with a length of fishing line, wire or the like 32. As shown in FIG. 6 the pin 24 comprises twin uprights joined at the top. This configuration provides good strength and stability.

A spring 34 is adjustably secured to the rigid back portion 20 by means of a peg 36 which is inserted into one of a number of corresponding apertures 38, which are arranged longitudinally along the rigid back portion 20. The spring 34 extends past the base of the pivoted pin 24 to a free end 30 of the pin to which it is secured (see FIG. 3).

In use, the finger splint 19 is secured to a user's hand with straps 40, which may be fixed with a hook and pile fastener, or a buckle or the like. Alternatively Velcro® straps may be used. The rigid back portion 20 is located on the back of a user's hand 22 and the finger sling 31 is placed over one of the user's fingers 26.

When the user exerts no force on the finger sling 31 with his finger 26, the finger splint 19 ideally assumes the configuration shown in FIG. 5, in which the pin 24 is substantially perpendicular to the rigid back portion 20 and the spring 34 is in a contracted state. The user's condition may prevent this ideal position though. The pin 24 has a stop 25 at its pivotally mounted base 42 to prevent the pin 24 being pulled beyond the point shown in FIG. 5 by the spring 34.

The lengths of the pin 24, the spring 34, the lever 28 and the length of wire 32 are chosen so that in the configuration shown in FIG. 5 the user's finger is approximately straight. The user's finger 26 is not pulled beyond straight by virtue of the stop 25 at the base 42 of the pin 24. The lever 28 has the effect of causing the finger sling 31 to be pulled directly away from the finger 26, rather than at an acute angle to the finger 26, which would result in the finger sling 31 being pulled along the user's finger 26. The length of the lever 28 can be varied to suit different sizes of finger.

When the user moves his fingers 26, the finger sling 31 pulls the pin 24 which moves about its base 42. As the pin 24 moves the spring 34 is stretched, as shown in FIG. 4.

The mode of operation can be best described with reference to FIG. 4. Two factors combine to significantly reduce the correcting force, which is applied to the finger 26. On the one hand, the extension of the spring 34 acts to restore the pin 24 to its original vertical position shown in FIG. 5. As the finger 26 is curled further, the extension of the spring is increased and accordingly that force acting to restore the pin 24 to its original position also increases. However, this does not automatically mean that the correcting force applied to the finger is increased because on the other hand, the angle θ° decreases, and therefore the component of the restoring force of the spring 34 transmitted through the pin 24 to the base increases. Accordingly, the force required to maintain the pin at a particular angle α° with respect to the base portion reduces as α° increases and θ° reduces. An equilibrium point is reached as shown in FIG. 3 whereat the force required to maintain the pin 24 at a particular angular orientation is minimised. As the pin rotates beyond this orientation, almost all of the restoring action of the spring 34 is transmitted through the pin 24 to the base portion 20 and only minimal force is required to overcome any restoring bending moment exerted by the spring 34 as a result of its contact over the pivot 25A as shown in FIG. 3. It will be noted that although the spring 34 is substantially parallel with the pin 24 in this figure, their lines of action are spaced apart, the line of action of the spring being above the pivot 25A such that the restoring force of the spring 34 on the pin 24 gives rise to a small anticlockwise moment M about said pivot which still acts to correct the attitude of the finger 26.

Consequently, once a user has moved the pivot pin beyond the equilibrium position when gripping an object, for instance when gripping a steering wheel, the user is able to maintain the grip for considerable periods of time with having to exert undegirably large forces in holding the spring 34 in an extended configuration. The base 42 of the pin 24 has a further stop (not shown) which prevents the pin 24 from moving too far.

In the manner described above, the finger splint 19 exerts a straightening tension on a finger inserted into the finger sling 31 whilst the finger is either straight or partially bent. When the finger 26 is bent (by roughly 80° to 90°) the tension on the finger 26 is much reduced by the interaction of the spring and the pin 24, thus allowing the user to grip an object for a reasonable period of time.

Additionally, the interaction of the spring 34 and the pin 24 results in an increase in the amount of tension on the finger 26 felt by the user as the finger 26 is moved from the position shown in FIG. 3 to the position shown in FIG. 5.

This is because the component of the restoring force of the spring carried by the pin is reduced as α° decreases and θ° increases, and therefore the force required to maintain the pin in a particular orientation increases.

The tension of the spring 34 may be adjusted by moving the peg 36 and inserting it into one of the other apertures 38, either further away from the base 42 of the pin 24 to increase the tension or nearer to the base 42 to reduce the tension.

The splint 19 described above shows only one finger sling 31. Further finger splints with corresponding springs and pins etc. could be fitted to the rigid back portion 20 to allow a number of fingers to be exercised at the same time.

The device could also be used to straighten a user's thumb, in which case a pair of pivot pins 24 and springs 34 would be provided which allow movement in two perpendicular planes. One plane could be the same as that of the finger movement described above with the other being at 900 to that to allow sideways movement also.

Other embodiments of the invention could comprise orthopaedic devices for straightening, or giving support to, a user's neck, in which case the user's "appendage" would be his head.

The applicant foresees that other embodiments not specifically described may be incorporated into the invention without exceeding its spirit or departing from the scope thereof, and these embodiments are considered as covered hereby.

What is claimed is:

1. A correction device for correcting the attitude of one or more digits of a hand from a curled position into a straight condition in which said digits extend away from the palm of said hand, said device comprising a base portion having means for securing the device to the hand behind the digits, said base portion having a front edge proximate the digits during use and a rear edge disposed at least partially around the hand behind the digits during use, a projection member pivotally attached to the base portion proximate the front edge of the base portion and having a longitudinal axis, a free end and a pivoting end;

a flexible sling depending from the free end of said projection member and adapted to support a digit therein;

a resilient member having a longitudinal axis, and being secured at a first end to said projection member at a position remote from the pivoting end of said projection member and at a second end to said base portion rearwardly of the pivotal attachment of said projection member to said base portion;

wherein the free end of said projection member is rotateable both towards and away from the rear edge of said base portion, rotation away from said rear edge causing elastic extension of the resilient member which exerts a force on said projection member which both resists said rotation and gives rise to a force moment about the pivotal attachment of said projection member which progressively decreases in magnitude as said free end of said projection member rotates away from the rear edge of said base and a digit supported by the sling connected to said projection member adopts positions with a greater degree of curl; and wherein the point of attachment of said resilient member to said base portion, the pivotal attachment of said projection member to said base portion, and the point of attachment of said resilient member to said projection are substantially aligned when the sling supports a digit which assumes the curled position thus substantially eliminating the force moment acting on the projection member to rotate the projection member back towards the rear edge of said base portion.

2. A correction device according to claim 1, wherein the rotation of the free end of the projection member towards the rear edge of the base portion is limited by stop means.

3. A correcting device according to claim 1 wherein the projection member comprises at least two upright sections which are joined at a free end thereof.

4. A correction device according to claim 1 wherein the attachment of the resilient member to the base portion can be made in plurality of locations rearwardly of the pivotal attachment of the projection member, the tension of the resilient member being increased as its attachment location of the base portion approaches rear edge thereof.

5. A correction device according to claim 1, wherein the resilient member is coiled spring.

6. A correcting device according to claim 1 wherein the device is arranged for use with a user's thumb.

7. A correction device according to claim 1, wherein the projection member terminates in an extension section to which the sling is connected, said resilient member being attached to said projection member immediately behind said extension section.

8. A correction device according to claim 7 wherein said extension section is perpendicular to the longitudinal axis of said projection member.

9. A correction device according to claim 1 wherein said means for securing the device to the hand includes straps, which have hook and pile fasteners secured thereto.

* * * * *

UNITED STATES PATENT AND TRADEMARK OFFICE
CERTIFICATE OF CORRECTION

PATENT NO. : 6,371,932 B1
DATED : April 16, 2002
INVENTOR(S) : Foote, Brian

It is certified that error appears in the above-identified patent and that said Letters Patent is hereby corrected as shown below:

Column 6,
Line 39, please change "the hand behind the digits during use, a projection member" to -- the hand behind the digits, during use a projection member --

Column 7,
Line 10, please change "3. A correcting device" to -- 3. A correction device --
Line 18, please change "of the base portion" to -- on the base portion --

Column 8,
Line 3, please change "6. A correcting device" to -- 6. A correction device --

Signed and Sealed this

Eighteenth Day of June, 2002

*Attest:*

JAMES E. ROGAN
*Director of the United States Patent and Trademark Office*

*Attesting Officer*